Figure 1:
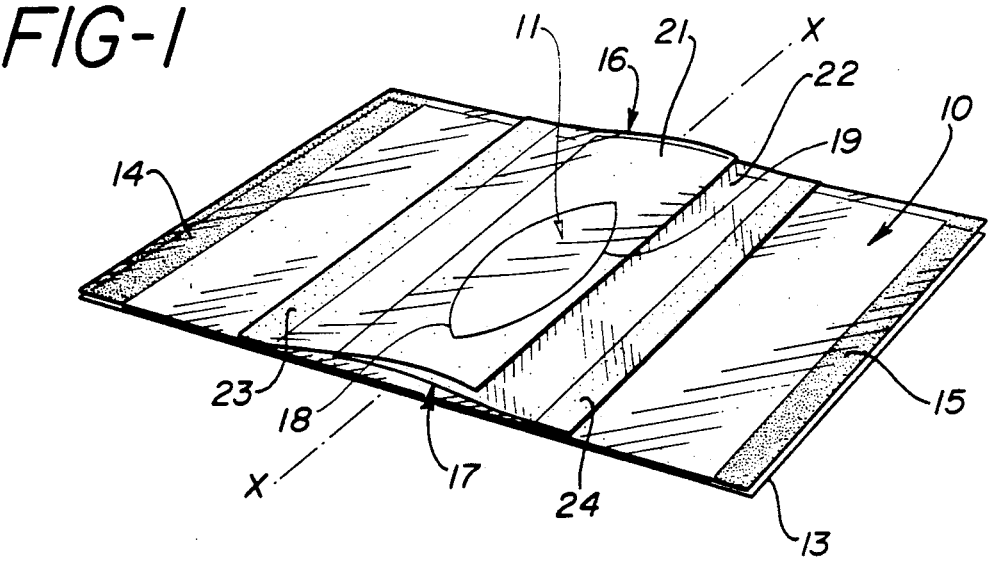

United States Patent [19]

Draeger

[11] Patent Number: 5,127,423
[45] Date of Patent: Jul. 7, 1992

[54] SURGICAL EYE COVER

[75] Inventor: Jörg Draeger, Hamburg, Fed. Rep. of Germany

[73] Assignee: Johnson & Johnson Medical, Inc., Arlington, Tex.

[21] Appl. No.: 586,117

[22] Filed: Sep. 21, 1990

[30] Foreign Application Priority Data

Sep. 23, 1989 [DE] Fed. Rep. of Germany ....... 3931803

[51] Int. Cl.⁵ .................. A61B 19/00; A61B 19/08
[52] U.S. Cl. .................................. 128/849; 128/854
[58] Field of Search ................... 128/849–856

[56] References Cited

U.S. PATENT DOCUMENTS

| | | | |
|---|---|---|---|
| 3,930,497 | 1/1976 | Krebs | 128/853 |
| 4,033,341 | 7/1977 | Scrivens | 128/852 |
| 4,275,720 | 6/1981 | Wichman | 128/853 |
| 4,323,062 | 4/1982 | Canty | 128/852 |
| 4,966,168 | 10/1990 | Glassman | 128/853 |

FOREIGN PATENT DOCUMENTS 0166124 1/1986 European Pat. Off. .

*Primary Examiner*—Robert A. Hafer
*Assistant Examiner*—Michael Brown

[57] ABSTRACT

A surgical eye cover for ophthalmological operations includes a first plastic film (10) to be applied to the face of a patient. The film has a window (11) cut in it to permit access to the patient's eye. A second, plastic film covers the window on the side away from the face. The second plastic film is made up of two cover flaps. Each flap is attached along one edge, generally parallel to each other, with the opposite, free edges directed toward each other, so that they overlap (20) over the window. The cover provides enhanced protection from contamination of the surgical site during eye surgery.

27 Claims, 2 Drawing Sheets

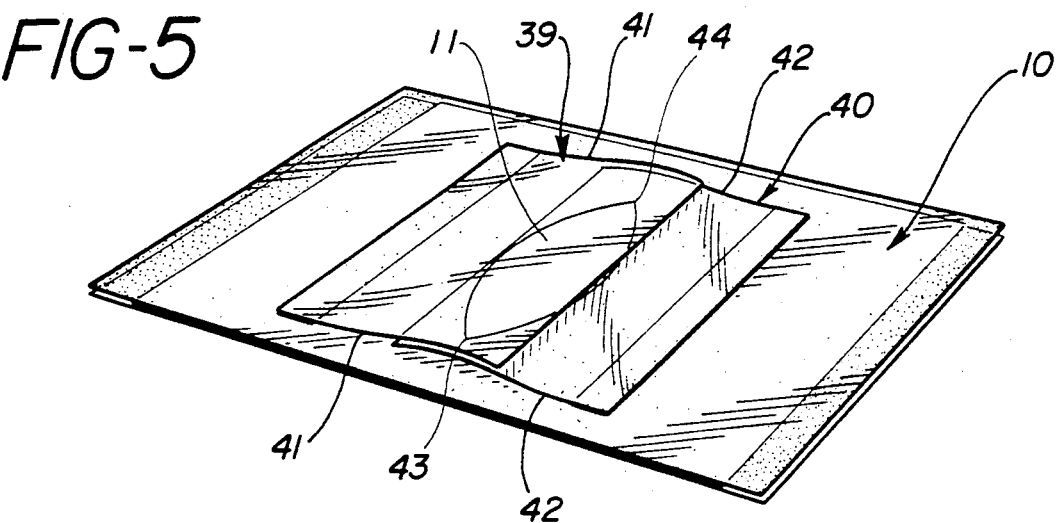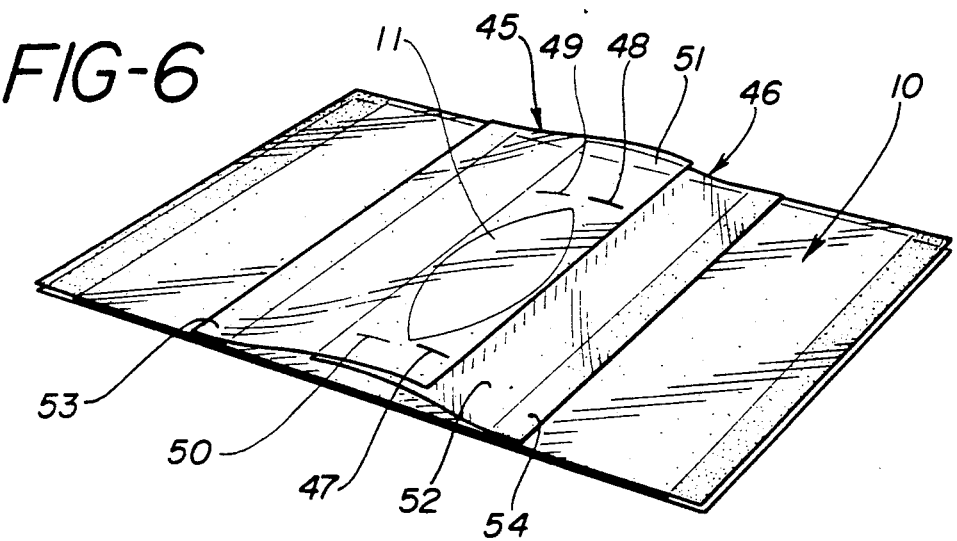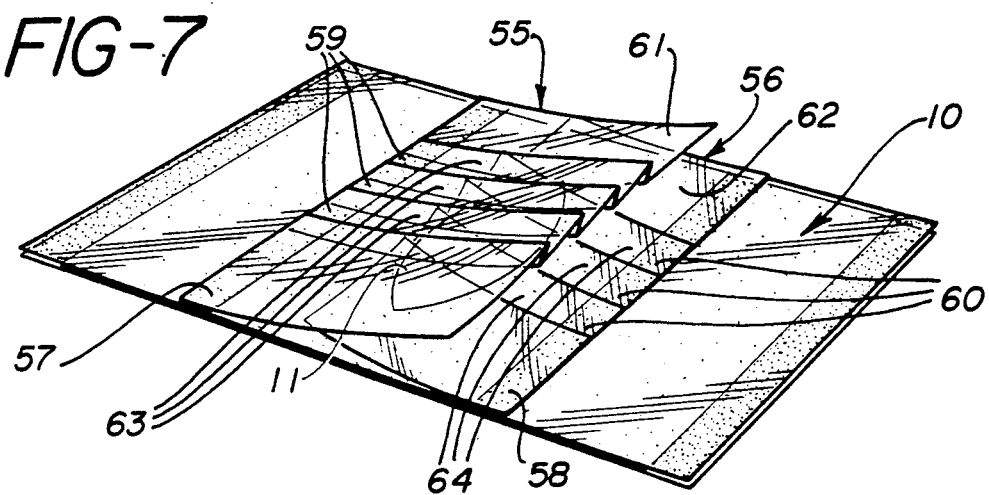

SURGICAL EYE COVER

The invention starts from a surgical eye cover according Patent EP 0 166 124 A2.

In order to perform microsurgical operations on the eye it is necessary, for hygienic reasons, to screen the region around the operation as carefully as possible from the region of operation. In the case of surgical eye covers of the abovementioned known type, the adhesive films which are normally used are opened before the start of the operation with a scissor-cut along the palpebral fissure in order to be able to cover the outside of the eyelids. However, it is the edges of the lids, which always have a burden of organisms, and less the outer surfaces of the lids, or the conjunctival sac, which may cause contamination of the region of operation, because the eyelashes or eyelash stumps which project below or beside the lid occlusion which is used are exposed.

Hence the invention has the object of improving the surgical eye cover of the abovementioned known type in such a way that, for the purpose of optimized hygienic preparation for the operation, it is possible for there to be complete covering of the edges of the lids with their eyelashes and eyelash stumps and, furthermore, covering of the inner side of the upper and lower lids with respect to the eyeball.

This object is achieved by the eye cover according to Patent EP0 166 124 A2.

The two cover flaps which overlap in the area of the window of the first plastic film make available sufficient material to cover the infection-bearing edges of the eyelids and thus to prevent the risk of contamination of the region of operation by the eyelashes or eyelash stumps which have a burden of organisms. At the same time, as previously, the top side of the eyelids is reliably covered. However, in addition, both the row of eyelashes and the outer and inner edge of the eyelids is also covered along the entire edge of the upper and lower lid during the entire duration of the operation. It is in fact possible, depending on the breadth of the freely drapable part of the cover flaps, for the inside of the upper and lower lid to be covered at least substantially with respect to the eyeball. The two cover flaps result not only in avoidance of the use of the preoperative film which has to be incised along the edge of the lid but also in the possibility of covering the edge of both eyelids over virtually the entire length when a lid occlusion is employed both on the upper and on the lower lid without a special action by the surgeon.

Embodiments of the invention are indicated in the subclaims.

In particular, there are various possible measures to be able to undertake the covering of the edges of the lids and inner sides of the lids in a straight-forward manner. Thus, the breadth of the longitudinal section, which covers the window, of at least one of the two cover flaps can be reduced or else have dimensions which are larger than the normal breadth of the relevant cover flap. In addition, the ability of the cover flaps to be modelled or draped can be further improved by the ends of the cover flap(s) projecting beyond the lateral contour edges or contour corners of the window and/or by the plastic film which forms the drapable part, which covers the window, of a cover flap being provided with folds by gathering in the area of fixing strips. In addition, the manipulability of the cover flaps can be rendered favorable by the particular choice of the material. Materials such as polyethylene, polyurethane or a copolymer of ethyl butylacrylate may be regarded as particularly suitable.

The fixing strips are provided for attachment to the first plastic film, preferably on the long edges, which are directed away from each other, of the two cover flaps. It is expedient in this connection for the distance of the fixing strips on the two cover flaps from each other to have dimensions greater than the distance between the contour edges, adjacent to them, of the window in the first plastic film. The fixing strips advantageously consist of a self-adhesive layer. This makes it possible to manufacture the eye cover economically.

The window can be designed and arranged appropriate for the purpose with regard to its contour, its size and position. Thus, for example, the window in the middle of a first plastic film, which is cut to be rectangular for example, can extend transverse to the longitudinal direction thereof and can, for example, be punched out from the first plastic film. The lower side of the first plastic film can be covered with a self-adhesive layer on which there is a protective film which can be removed before the eye cover is put to use. The manipulation of the eye cover can be further improved by designing the two narrow sides of the first rectangular plastic film as gripping tabs free from the self-adhesive layer. It is preferable for the cover flaps and/or the first plastic film to be 15 to 50 μm thick and, if possible, transparent. This further facilitates the manipulability of the eye cover.

The invention is described in more detail hereinafter with the aid of the diagrammatic drawing of several exemplary embodiments.

Figure 2:
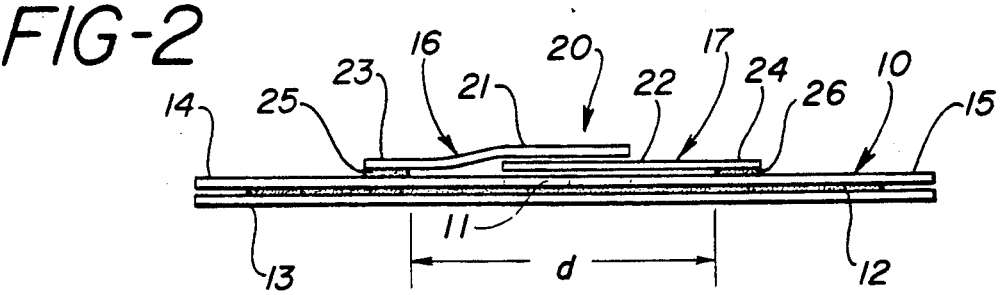

FIG. 1 shows a perspective view of a first embodiment of a surgical eye cover with cover flaps which have equal breadth dimensions over the entire length, FIG. 2 shows a front view of the surgical cover film in FIG. 1.

Figure 3:
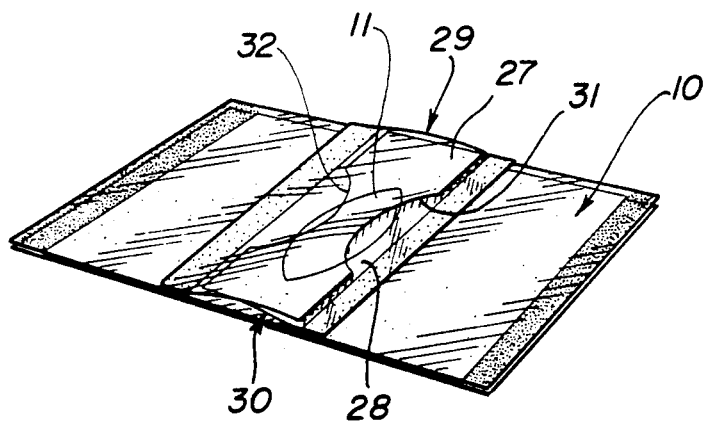
Figure 4:
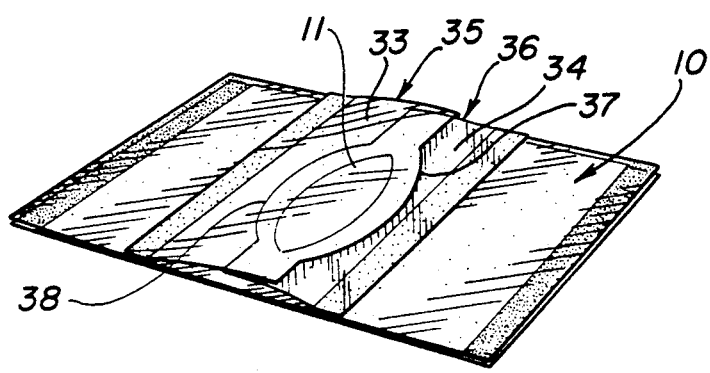

FIG. 3 shows a perspective view of a second embodiment of a surgical eye cover in which the breadth of the cover flaps is reduced in the area of the window in the first plastic film located thereunder, FIG. 4 shows a perspective representation of a third embodiment of a surgical eye cover in which the breadth of the cover flaps is widened in the area of the window in the first plastic film located thereunder, FIG. 5 shows a perspective view of a fourth embodiment of a surgical eye cover with cover flaps which are arranged only in the area of the window, FIG. 6 shows a perspective view of a fifth embodiment of a surgical eye cover with cover flaps which are transversely incised on both sides of the window, and FIG. 7 shows a perspective view of a sixth embodiment of a surgical eye cover in which the cover flaps have transverse folds in the area of the window.

FIG. 1 and 2 depict a surgical eye cover for microsurgical ophthalmological operations, which consists of a first rectangular plastic film 10 which is to be applied on the face of a patient. If desired, the plastic film 10 can also be cut to any other shape, in place of rectangular, which is appropriate for the purpose. A window 11 is cut in this first plastic film 10, for example by punching, and its contour corresponds at least to the size and shape of the visible part of the eyeball of an infant. However, a possible deviation from this is for the window 11 also to be circular, elliptical, oval, rectangular etc. The window 11 ought, however, to have a size of at least 1.5 cm². The lower side, which is directed towards the face of the patient, of the first plastic film 10 is coated with a self-adhesive layer 12 which is covered by a removable protective film 13 (FIG. 2). The two narrow sides of the first plastic film 10 can be designed as free gripping tabs 14 and 15 in order to facilitate grasping of the first plastic film 10 and removal of the protective film 13. It is also possible, where appropriate, for the gripping tabs 14, 15 to be provided on the long sides of the first plastic film 10 which, in place of a rectangular shape, can have, for example, also the shape of an ellipse.

Two cover flaps 16, 17 covering the window 11 are attached on the top side, which is directed away from the face of the patient, of the plastic film 10 and consist of a thin plastic film, which can easily be modelled or draped, of the same material, where appropriate, as the first plastic film 10. There is attachment of the first, upper cover flap 16 in the area of the upper contour edge 18 of the window 11, and of the second, lower cover flap 12 in the area of the lower contour edge 19 of the window 10 11, approximately parallel to the long axis x—x thereof. The cover flaps 16, 17 overlap at 20, with their freely drapable parts 21, 22 directed towards each other, over the window 11 so that at least the inner and outer edges of the upper and lower lid can be covered over the entire length. It is preferable for the breadth of the overlap 20 to have dimensions of such a size that the inner side of the upper and lower lid can also be covered at least substantially, preferably completely, with respect to the eyeball. The breadth of the overlap 20 of the freely drapable parts 21, 22 of the cover flaps 16, 17 is preferably 10-20 mm. The breadth of the freely drapable parts 21, 22 of the two cover flaps 16, 17 in the described exemplary embodiment is at least 16 mm. The material to be preferred for the cover flaps 16, 17 and for the first plastic film 10 is, in particular, polyethylene, polyurethane or a copolymer of ethyl butylacrylate, although all transparent and water-repelling materials which have an ability to be modelled and draped suitable for this purpose can be employed.

The long edges, which are directed away from each other, of the two cover flaps 16, 17 are in each case designed as fixing strips 23, 24 for attachment to the first plastic film 10. The distance d of the fixing strips 23, 24 of the two cover flaps 16, 17 has dimensions greater than that between the two contour edges 18, 19 of the window 11. The distance of the fixing strips 23, 24 from the associated contour edge 18, 19 of the window 11 should, moreover, be from 1 to 20 mm. The distance d between the fixing strips 23, 24 of the two cover flaps 16, 17 should be at least 17 mm. The fixing strips 23, 24 of the cover flaps 16, 17 are, moreover, at least 1 mm wide. The fixing strips 23, 24 preferably consist of a self-adhesive layer 25, 26 on the lower side of the cover flaps 16, 17 in the area of their long edges directed away from each other. A possible deviation from this is also, where appropriate, to choose other types of attachment such as, for example, heat-sealing.

The thickness of the first plastic film 10 and of the two cover flaps 16, 17 is preferably less than 15 μm. It is furthermore preferred for the first plastic film 10 and the two cover flaps 16, 17 to be produced from transparent material.

Most of the features of the first embodiment of a surgical eye cover described above in connection with FIGS. 1 and 2 also apply to the embodiments depicted in FIGS. 3 to 7.

However, in FIG. 3 the breadth of the drapable parts of two cover flaps on a middle longitudinal section covering the window 11 has narrower, and in FIG. 4 wider, dimensions than the remaining width of these drapable parts of the cover flaps.

Thus, it can be seen in FIG. 3 that the drapable part 27, 28 of an upper and lower cover flap 29, 30 is provided, at the free long sides, with a curved cut-out 31, 32 in each case. This embodiment serves to facilitate covering of the upper and lower eyelid edges.

In contrast thereto, the drapable part 33, 34 of an upper and of a lower covering flap 35, 36 has, in the case of the surgical eye cover in FIG. 4, wider dimensions in the area of the window 11, with the broadening of the drapable parts 33, 34 being formed by a projecting curved flap 37, 38 in each case. This embodiment is particularly provided for the case where the intention is to cover not only the outer sides and edges of the upper and lower eyelid but also the inner sides thereof, as completely as possible with respect to the eyeball. In this case there is sufficient material available for the cover flaps 35, 36 to be wrapped around the edges of the lids in the area of the window 11 when a lid occlusion is employed to such an extent that the inner side of the eyelids can, at least substantially, be covered by the cover flaps also in the areas of the eye socket in which they can be lifted furthest from the eyeball.

Since sufficient material of the cover flaps must be available for it to be possible more easily to fold them around the edges of the lids as completely as possible on the inner side of the eyelids, it is also possible, according to FIG. 5, for one or both cover flaps 39, 40 to project with their ends 41, 42 in each case beyond the contour corners 43, 44 of the window 11 so that they lie at a great distance from the adjacent edges of the plastic film.

According to FIG. 6, one or both cover flaps 45, 46 can be at least partially incised on both sides or contour edges 43, 44 of the window 11 transverse to the longitudinal direction of the cover flaps 45, 46. These incisions 47, 48 and 49, 50 in the upper and lower drapable part 51, 52, respectively, of the cover flaps 45, 46 extend from their free long edge to approximately their longitudinal middle. Of course, it is also possible for the incisions 47, 48 and 49, 50 to continue up to the fixing strips 53, 54. The incisions can, as in FIG. 6, be straight-line but also, where appropriate, curved.

It is additionally possible, as FIG. 7 shows, for the material of one or both cover flaps 55, 56 in the area of the window 11 to be gathered on the associated fixing strips 57, 58 transverse to the longitudinal direction of the latter at 59 and 60, respectively, in such a way that the drapable part 61, 62 of the cover flaps 55, 56 in the area of the window 11 has so many folds 63, 64 that the material additionally available due to the folds is suitable to cover the larger area, caused by the curvature of the eyeball, between the inner side of an eyelid, in particular the upper eyelid, and the eyeball while avoiding formation of folds.

It is self-evident that the breadth of the two cover flaps, in particular of their part which can be freely draped and modelled, can have different dimensions. Thus, for example, the drapable part of the upper cover flap can be wider than that of the lower cover flap so that the area of the inner side of the upper eyelid, which is larger in comparison with the lower eyelid, can be covered as completely as possible with respect to the eyeball. It is also possible in this connection for the cover flaps to be designed to be tongue-shaped in order to be able to introduce the tip of the tongue as high as possible into the eye level. Furthermore, the surgical eye cover can be an integral constituent of a part- or whole-body cover for patients.

The above description demonstrates that this surgical eye cover provides the possibility, in a straightforward manner, when a lid occlusion is employed, of simultaneously wrapping the cover flaps around the edges of the eyelids on their inner side and thus protecting the region of operation from contamination by the edges of the lids, which always have a burden of organisms, and the eyelashes or eyelash stumps thereof.

I claim:

1. Surgical eye cover for ophthalmological operations, which consists of a first plastic film (10) which is to be applied on the face of a patient and has a window (11) whose upper contour edge (18) is adjacent to the upper eyelid and whose lower contour edge (19) is adjacent to the lower eyelid, and a second plastic film which covers the window (11) of the first plastic film (10) on its top side directed away from the face, characterized in that the second plastic film is made up of two cover flaps (16, 17; 29, 30; 35, 36; 39, 40; 45, 46; 55, 56), of which the first cover flap (16; 29; 35; 39; 45; 55) in the area of the upper contour edge (18) of the window (11) and the second cover flap (17; 30; 36; 40; 46; 56) in the area of the lower contour edge (19) of the window (11) are attached to the first plastic film (10) and are arranged approximately parallel to each other and, with their freely drapable parts (21, 22; 27, 28; 33, 34; 51, 52; 61, 62) directed towards each other, overlap (at 20) over the window (11) so that at least the inner and outer edges of the upper and lower lid can be covered over the entire length.

2. Surgical eye cover according to claim 1, characterized in that the breadth of the overlap (20) of the two cover flaps (16, 17; 29, 30; 39, 40; 45, 46; 55, 56) has dimensions of such a size that in each case the inner side of the upper lid and lower lid can be covered with respect to the eyeball.

3. Surgical eye cover according to claim 1, characterized in that the breadth of the overlap (20) of the cover flaps (16, 17; 29, 30; 35, 36; 39, 40; 45, 46; 55, 56) is 10 to 20 mm.

4. Surgical eye cover according to claim 1, characterized in that the breadth of the freely drapable part (21, 22; 27, 28; 33, 34; 51, 52; 61, 62) of the two cover flaps (16, 17; 29, 30; 35, 36; 39, 40; 45, 46; 55, 56) is at least 16 mm.

5. Surgical eye cover according to claim 1 characterized in that the breadth of the freely drapable part (27, 28) of the cover flaps (29, 30) is reduced in the area of the window (11).

6. Surgical eye cover according to claim 5, characterized in that the freely drapable part (27, 28) of the two cover flaps (29, 30) is provided, at its free long side in the area of the window (11), with a curved cutout (31, 32).

7. Surgical eye cover according to claim 1 characterized in that the breadth of the freely drapable part (33, 34) of the two cover flaps (35, 36) is widened in the area of the window (11).

8. Surgical eye cover according to claim 7, characterized in that the widening is formed in each case by a curved projecting tab (37, 38) on the free long side.

9. Surgical eye cover according to claim 1 characterized in that the cover flaps (16, 17; 29, 30; 35, 36; 39, 40; 45, 46; 55, 56) extend up to the opposing side edges of the first plastic film (10).

10. Surgical eye cover according to claim 9, characterized in that the drapable part (51, 52) of the two cover flaps (45, 46) is provided, in the area of the right and left contour edges and corners (43, 44) of the window (11), with a transverse incision (47, 48; 49, 50).

11. Surgical eye cover according to claim 1 characterized in that the ends (41, 42) of the cover flaps (39, 40) project over the sides (contour corners 43, 44) of the window (11) and are arranged at a distance from the adjacent edges of the first plastic film (10).

12. Surgical eye cover according to claim 1 characterized in that in each case fixing strips (23, 24; 53, 54; 57, 58) for attaching to the first plastic film (10) are mounted on the long edges of the two cover flaps (16, 17; 29, 30; 35, 36; 39, 40; 45, 46; 55, 56) directed away from each other.

13. Surgical eye cover according to claim 12, characterized in that, in order to form folds (63, 64) in the drapable part (61, 62), the plastic film, which forms the drapable part (61, 62) of the cover flaps (55, 56) which covers the window (11), is gathered (at 59, 60) in the area of the fixing strips (56, 58) in the longitudinal #3 direction thereof.

14. Surgical eye cover according to claim 12 characterized in that the fixing strips (23, 24; 53, 54; 57, 58) of the two cover flaps (16, 17; 45, 46; 55, 56) are arranged at a greater distance from each other than the adjacent contour edges (18, 19) of the window (11).

15. Surgical eye cover according to claim 14, characterized in that the distance of the fixing strips (23, 53, 54; 57, 58) from the associated contour edge (18, 19) of the window (11) is between 1 and 20 mm.

16. Surgical eye cover according to claim 12 characterized in that the distance between the fixing strips (23, 24; 53, 54; 57, 58) of the two cover flaps (16, 17; 45, 46; 55, 56) is at least 17 mm.

17. Surgical eye cover according to claim 12 characterized in that the fixing strips (23, 24; 53, 54; 57, 58) of the cover flaps (16, 17; 45, 46; 55, 56) are at least 1 mm wide.

18. Surgical eye cover according to claim 12 characterized in that the fixing strips (23, 24; 53, 54; 57, 58) consist of a self-adhesive layer (25, 26).

19. Surgical eye cover according to claim 1 characterized in that the cover flaps consist of polyethylene.

20. Surgical eye cover according to claim 1, characterized in that the cover flaps consist of polyurethane.

21. Surgical eye cover according to claim 1, characterized in that the cover flaps consist of an ethylene/butyl acrylate copolymer.

22. Surgical eye cover according to claim 1 characterized in that the first plastic film (10) is rectangular and the window (11) in the middle of the first plastic film extends transverse to the longitudinal direction thereof.

23. Surgical eye cover according to claim 1 characterized in that the window (11) is punched out from the first plastic film (10).

24. Surgical eye cover according to claim 1 characterized in that the first plastic film (10) can be modelled and is provided on the lower side with a self-adhesive layer (12) which is covered by a removable protective film (13).

25. Surgical eye cover according to claim 1 characterized in that two opposing sides of the first plastic film (10) are designed as gripping tabs (14, 15) free from the self-adhesive layer (12).

26. Surgical eye cover according to claim 1 characterized in that the first plastic film (10) and/or the cover flaps (16, 17; 29, 30; 35, 36; 39, 40; 45, 46; 55, 56) are less than 50 μm thick.

27. Surgical eye cover according to claim 1 characterized in that the first plastic film (10) and/or the cover flaps (16, 17; 29, 30; 35, 36; 39, 40; 45, 46; 55, 56) are transparent.

* * * * *